United States Patent
Gershon

(10) Patent No.: US 8,158,615 B2
(45) Date of Patent: Apr. 17, 2012

(54) ANTI-VIRAL COMPOSITION FOR THE TOPICAL TREATMENT OF HERPES LABIALIS (COLD SORES) AND METHOD FOR USE THEREOF

(75) Inventor: David Gershon, New York, NY (US)

(73) Assignee: Redox PHARMACEUTICAL Corporation, Greenvale, NY (US)

( * ) Notice: Subject to any disclaimer, the term of this patent is extended or adjusted under 35 U.S.C. 154(b) by 881 days.

(21) Appl. No.: 11/762,542

(22) Filed: Jun. 13, 2007

(65) Prior Publication Data

US 2007/0299045 A1    Dec. 27, 2007

Related U.S. Application Data

(60) Provisional application No. 60/805,921, filed on Jun. 27, 2006.

(51) Int. Cl.
*A61K 31/555* (2006.01)
*A61K 9/00* (2006.01)

(52) U.S. Cl. .................................. 514/185; 424/400

(58) Field of Classification Search ................... 514/185
See application file for complete search history.

(56) References Cited

U.S. PATENT DOCUMENTS 5,756,491 A * 5/1998 Dori ............................ 514/185

OTHER PUBLICATIONS

The Merck Manual, Fifteenth Edition, 1987, 180-181, 2327-2328.*

* cited by examiner

*Primary Examiner* — Shengjun Wang
(74) *Attorney, Agent, or Firm* — Jules E. Goldberg

(57) ABSTRACT

A composition for the treatment of Herpes Labialis which contains CTC-96 as the active ingredient is disclosed. Methods for using the composition are also disclosed. The composition may be used as a topical ointment.

1 Claim, 1 Drawing Sheet

Antiviral activity of CTC-96 in Dermal Ointment Formulation

CTC-96 extracted from Dermal Ointment Formulation or CTC-96 in PBS were assayed for antiviral activity. Results are presented as % inhibition ± standard deviation.

Antiviral activity of CTC-96 in Dermal Ointment Formulation
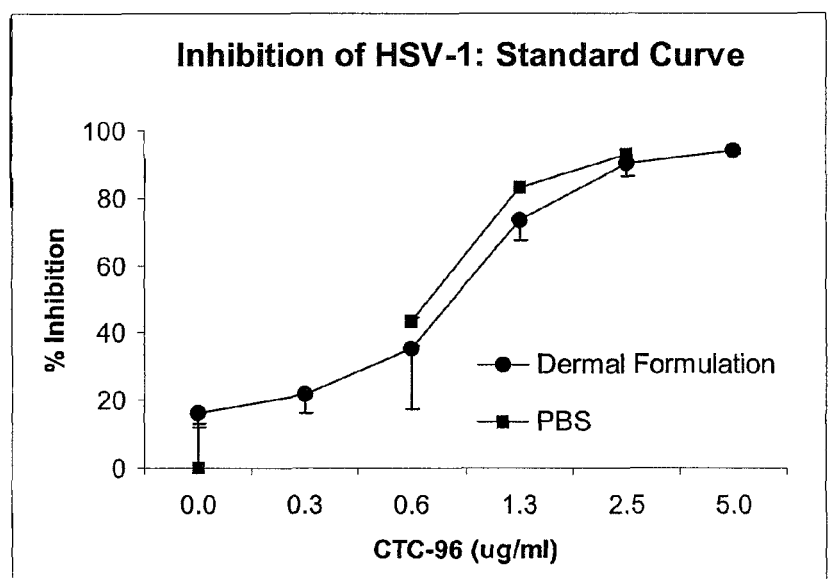
CTC-96 extracted from Dermal Ointment Formulation or CTC-96 in PBS were assayed for antiviral activity. Results are presented as % inhibition ± standard deviation.

ANTI-VIRAL COMPOSITION FOR THE TOPICAL TREATMENT OF HERPES LABIALIS (COLD SORES) AND METHOD FOR USE THEREOF

RELATIONSHIP TO OTHER APPLICATIONS

This application is based on Provisional Application Ser. No. 60/805,921 filed Jun. 27, 2006, the priority of which is hereby claimed.

BACKGROUND OF THE INVENTION

1. Field of the Invention

This invention relates to the field of methods for the treatment of Herpes Facialis which is a recurrent disease characterized by episodic vesicular eruptions on the lips and perioral skin.

2. Description of Related Art

This disease is Oro-facial Herpes Labialis and is a Herpes Virus infection, also known in the vernacular as cold sores, sun sores, or fever blisters. Oro-facial Herpes Labialis is caused predominantly by Herpes Simplex Virus Type-1 (HSV-1), with a minor subset of patients infected with HSV-2. While oro-facial infection with HSV-2 is possible, recurrent HSV-2 eruptions are rare. Initial infection with Herpes Simplex Virus Type-1 (HSV-1) generally causes mild or negligible symptoms. Herpes Labialis (HSV-1) is characterized by a high rate of recurrences, most often at the site of initial infection (recurrent Herpes Labialis). In the United States 40-50% of the adolescent population and 80-90% of the adult population has been exposed to HSV-1 (1). Approximately 40% of the infected population has had a cold sore at one time or another (2) and most people who have had cold sores will have recurrent outbreaks. Over 50 million adults in the United States have 2 or more outbreaks per year. Episodes generally regress within 7-10 days with complete healing by 12-14 days although a flat scar or erythema may persist (3). While recurrent Herpes Labialis is a benign disease that regresses spontaneously, it is highly contagious with high viral titers in blisters and effluent. Herpes Labialis causes physical pain and can also be disfiguring especially in those patients with frequent recurrences (3).

Current treatments for Herpes Labialis can be divided into three major categories: 1) palliative treatment 2) topical antiviral medication 3) systemic antiviral medication. Palliative treatments with numbing agents (lidocaine, tetracaine, benzocaine, benzyl alcohol, camphor, and phenol) and emollients (petrolatum and allantoin) while alleviating some of the discomfort of a recurrence of Herpes Labialis have no effect on the time course or on the frequency of recurrences. There are several topical and systemic antiviral medications that purport to shorten the time course of Herpes Labialis eruptions. Abreva® (docosanol 10% Cream formula), a topical cream which has been approved by the FDA for over the counter (OTC) sale, interferes with the adsorption of virus to cell surface lipid membranes but not with the binding of virions to the cell surface (4). Abreva® (docosanol), which has not been shown to have any direct anti-viral activity (5), has been shown to shorten mean healing time from 7.3 to 5.7 days. For significant response, docosanol must be applied during the prodrome. The prescription antiviral drugs, Zovirax® (acyclovir), Valacyclovir®, penciclovir, and famciclovir used for HSV-1 infections are all analogs of acyclic guanosine. The FDA has not approved these drugs for OTC sale because of possible development of viral resistance (6). Due to low bioavailability, Zoviraxe has but marginal efficacy and application after the prodromal phase has little or no efficacy (7). Treatment with penciclovir in 1% concentration (Denavir® 1%) when started during the prodrome is more effective than Zovirax® in decreasing lesion healing time, alleviation of pain, and viral shedding (7;8). However, application after the prodromal phase has but marginal efficacy with 20-30% reduction in symptoms and time to healing (7). Famvir® (famciclovir) is converted to penciclovir in the body. Famciclovir is active against the same viruses as Acyclovir but has a longer duration of action. Valacyclovil, a valine ester of acyclovir, is another "prodrug," which is converted to acyclovir in the body. Oral Valtrex® (Valacyclovir) is approved for use in immunocompetent adults as a one day treatment. Oral treatment with these acyclovir produgs shortens duration of Herpes Labialis episodes by approximately 1 day (9).

None of the current topical treatments for HSV-1 infection have proven to be completely effective and no cure is available.

SUMMARY OF THE INVENTION

I have discovered a method for the successful treatment of Herpes Labialis (cold sores). I have found that the application of a compound known as CTC-96 to the cold sore can substantially mediate both the severity and duration of the cold sore. CTC-96 is known to be a very efficient anti-HSV-1 drug as attested by ocular studies in animals (4) and is safe at efficacious doses in human eyes

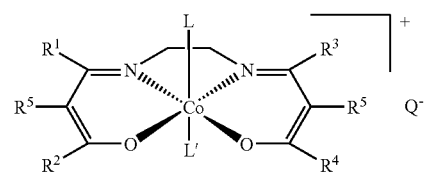

wherein $R_1$, $R_2$, $R_3$ and $R_4$ are methyl, $R_5$ are each hydrogen and L and L' are each:

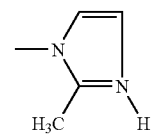

and Q' is Br⁻.

CTC-96 may be prepared by the method described in the U.S. Pat. No. 5,756,491, the contents of which are hereby incorporated by reference.

I have further discovered a dermal formulation containing CTC-96 wherein the active ingredient penetrates only into the epidermis with exceptionally low systemic penetration.

BRIEF DESCRIPTION OF THE DRAWING

FIG. 1 is a graphical representation showing the anti-viral activity of CTC-96 extracted from the dermal formulation.

DETAILED DESCRIPTION OF THE INVENTION

Accordingly I have discovered that subjects infected with Herpes Simplex Virus Type-1 (HSV-1) and Herpes Simplex Virus Type-2 (HSV-2) may be therapeutically treated to decrease the severity and duration of the Herpes Labialis by administering an anti-HSV-1 and HSV-2 effective amount of the compound CTC-96 to a subject infected with the disease. The compound may be administered topically, intramuscularly or orally. The drug is very active against HSV-1 and HSV-2 in the micromolar range of concentrations, particularly for its dermal manifestations. It prevents HSV-1 and HSV-2 penetration into cells and also cell-cell transmission of the virus (14). It thus reduces viral yields and the severity of Oro-facial Herpes Labialis and considerably accelerates the cure of the disease. Moreover, since the drug has a unique mode of action in binding to imidazole groups of histidines in proteins and does not involve DNA synthesis, it will act against current and emerging strains of HSV-1 and HSV-2 which are drug resistant to the known anti-viral drugs, e.g., acyclovir, penciclovir, cidofovir, ganciclovir and idoxuridine. In addition, the drug reduces inflammatory reactions to the virus infection and thus lowers or eliminates the severity of the symptoms.

Because HSV-1 propagates in the epidermis of the skin, CTC-96 is a valuable and safe drug in a topical formulation for cutaneous viral infections. This compound was approved by FDA for phase 2 studies in human eyes. The drug has a unique mode of action in that it inactivates certain proteins by binding to the imidazole of specific histidines (10) and possesses activity due to the superoxide scavenging capacity of the compound (11) in addition to anti-viral efficacy. It has both an anti-microbial activity and a therapeutic effect on HSV-1. Because of its unique mode of action the drug is effective against drug-resistant strains of HSV-1 which have become a problem in the control of the virus.

The percutaneous absorption of Doxovir-L® (CTC-96) was evaluated by mixing CTC-96 at two concentrations (10 mg/g and 1 mg/g) to homogeneity with a Dermal ointment Formulation (petrolatum 10% by weight, camphor 0.92% by weight, menthol 0.5% by weight, methyl salicylate 0.26% by weight, eucalyptus oil 0.30% by weight) and was determined in vitro, using the human cadaver skin model using the finite dose technique and Franz Diffusion Cells (12;13). Placebo consisted of the drug formulation without drug. The amount of Dermal ointment that is applied at each treatment was determined is shown in the following table (TABLE 1):

TABLE 1

| Subject | Amount of Dermal Ointment Applied/10 cm² (mg) | Average Amount of Dermal Ointment Applied/10 cm² (mg) |
|---|---|---|
| V.S | 19.6 | 18.0 |
|  | 16.6 |  |
| D.T. | 27.4 | 27.4 |
|  | 27.4 |  |
| Average |  | 22.7 |

The percutaneous absorption of Doxovir-L® (CTC-96) was determined is shown in the following table (TABLE 2 & TABLE 3):

TABLE 2

Percutaneous Absorption of CTC-96 through Human Cadaver Skin over 48 hours from a Single Application: Percent of Applied Dose*

|  | Drug concentration | | |
|---|---|---|---|
| Sample Source | 10 mg/g | 1 mg/g | Blank controls |
| Receptor Solution | 0 | 0 | 0 |
| Dermis | 0 | 0 | 0 |
| Epidermis | 3.63 ± 0.58 | 2.20 ± 1.09 | 0 |

TABLE 2-continued

Percutaneous Absorption of CTC-96 through Human Cadaver Skin over 48 hours from a Single Application: Percent of Applied Dose*

|  | Drug concentration | | |
|---|---|---|---|
| Sample Source | 10 mg/g | 1 mg/g | Blank controls |
| Stratum Corneum** | 1.29 ± 0.67 | 0.06 ± 0.06 | 0 |
| Surfacewash | 10.81 ± 3.79 | 7.41 ± 0.30 | 0 |
| Total Recovery | 15.72 ± 3.12 | 9.67 ± 1.34 | 0 |

*(Mean ± SE, n = 3 Donors, in triplicate).
**Stratum Corneum was measured from the Tape Strip samples

TABLE 3

Percutaneous Absorption of CTC-96 through Human Cadaver Skin over 48 hours from a Single Application: Mass (µg/cm2)*

|  | Drug concentration | | |
|---|---|---|---|
| Sample Source | 10 mg/g | 1 mg/g | Blank controls |
| Receptor Solution | 0 | 0 | 0 |
| Dermis | 0 | 0 | 0 |
| Epidermis | 1.81 ± 0.29 | 0.11 ± 0.05 | 0 |
| Stratum Corneum** | 0.64 ± 0.33 | 0.03 ± 0.00 | 0 |
| Surface wash | 5.41 ± 1.90 | 3.17 ± 0.01 | 0 |
| Total Recovery | 7.86 ± 1.56 | 4.83 ± 0.07 | 0 |

*(Mean ± SE, n = 3 Donors, in triplicate).
**Stratum Corneum was measured from the Tape Strip samples These studies indicate penetration of CTC-96 only into the epidermis with exceptionally low dermal and thus possible systemic penetration (based on the dermal and receptor solution data). Because HSV-1 propagates in the epidermis of the skin CTC-96 is a valuable and safe topical formulation for cutaneous viral infections.

The CTC-96 exhibits excellent in vitro stability and efficacy in dermal formulation as shown by the following (TABLE 4 & TABLE 5):

CTC-96 was mixed to homogeneity with a Dermal Ointment Formulation (petrolatum 10% by weight, camphor 0.92% by weight, menthol 0.5% by weight, methyl salicylate 0.26% by weight, eucalyptus oil 0.30% by weight).

TABLE 4

Stability CTC-96 In Dermal Ointment Formulation
Recovery of CTC-96 from CTC-96 incubated in in Dermal ointment Formulation

|  |  | Incubation for: | | |
|---|---|---|---|---|
|  |  | 0 Time | 12 weeks | 6 months |
| Drug | Incubation Temperature | % Recovery Mean ± SD | % Recovery Mean ± SD | % Recovery Mean ± SD |
| Placebo | 4° C. | 0.0 | nd | nd |
| CTC-96 10 mg/ml | 4° C. | 103.5 ± 3.8 | 92.3 ± 0.7 | 110.2 ± 4.8 |
| Placebo | 40° C. | 0.0 | nd | nd |
| CTC-96 10 mg/ml | 40° C. | 104.0 ± 0.9 | 92.9 ± 4.2 | 112.2 ± 4.1 |
| CTC-96 Drug standard |  | 100.0 | 100.0 | 100.0 |

TABLE 5

Recovery of CTC-96 Anti-viral Activity from CTC-96 incubated in Dermal Ointment Formulation

| Incubation Time | % Inhibition* | |
|---|---|---|
| | 4° C. Mean ± SD | 40° C. Mean ± SD |
| 0 | 91.8 ± 1.7 | 88.8 ± 2.7 |
| 3 mo | 91.5 ± 0.5 | 90.1 ± 0.8 |
| 6 mo | 91.5 ± 3.4 | 92.1 ± 1.0 |
| Placebo | 9.9 ± 11.0 | −10.3 ± 3.4 |

*CTC-96 extracted from Dermal Ointment Formulation was diluted to 2.5 µg/ml and assayed for antiviral activity. Results are presented as % inhibition ± standard deviation.

Reference List

1. Smith, J. S. and Robinson, N. J. (2002): Age-specific prevalence of infection with herpes simplex virus types 2 and 1: a global review. *J. Infect. Dis.*, 186 Suppl 1:S3-28.
2. Crumpacker, C. S. and Guelic, R. M. (1999): Herpes Simplex. In: *Fitzpatrick's Dematology in General Medicine*, edited by I. M. e.a. Freedberg, pp. 2414-2426. McGraw-Hill, Inc., New York.
3. Spruance, S. L., Overall, J. C., Jr., Kern, E. R., Krueger, G. G., Pliam, V., and Miller, W. (1977): The natural history of recurrent herpes simplex labialis: implications for antiviral therapy. *N. Engl. J Med.*, 297:69-75.
4. Pope, L. E., Marcelletti, J. F., Katz, L. R., Lin, J. Y., Katz, D.H., Parish, M. L., and Spear, P. G. (1998): The anti-herpes simplex virus activity of n-docosanol includes inhibition of the viral entry process. *Antiviral Res*, 40:85-94.
5. McKeough, M. B. and Spruance, S. L. (2001): Comparison of new topical treatments for herpes labialis: efficacy of penciclovir cream, acyclovir cream, and n-docosanol cream against experimental cutaneous herpes simplex virus type 1 infection. *Arch. Dermatol.*, 137:1153-1158.
6. Guidance for industry. *OTC treatment of herpes labialis with antiviral agents. US Department of Health and Human Services, FDA, CDER*; March 2000. Available at: www.fda.gov/cder/guidance/3571dft.pdf. 2000. (GENERIC) Ref Type: Data File
7. Femiano, F., Gombos, F., and Scully, C. (2001): Recurrent herpes labialis: efficacy of topical therapy with penciclovir compared with acyclovir (aciclovir). *Oral Dis.*, 7:31-33.
8. Anonymous (1997): Topical penciclovir for herpes labialis. *Med. Lett. Drugs Ther.*, 39:57-58.
9. Jensen, L. A., Hoehns, J. D., and Squires, C. L. (2004): Oral antivirals for the acute treatment of recurrent herpes labialis. *Ann. Pharmacother.*, 38:705-709.
10. Louie, A. Y. and Meade, T. J. (1998): A cobalt complex that selectively disrupts the structure and function of zinc fingers. *Proc. Natl. Acad. Sci U.S.A.*, 95:6663-6668.
11. Wooley, P. H. and Whalen, J. D. (1992): The influence of superoxide scavenging compound CTC 23 on type II collagen-induced arthritis in mice. *Agents Actions*, 35:273-279.
12. Franz, T. (1978): The finite dose technique as a valid in vitro model for the study of percutaneous absorption in man. In: *Skin: Drug Application and Evaluation of Environmental Hazards, Current Problems in Dermatology*, edited by G. Simon, et al, pp. 5868S. Karger,
13. Franz, T. (1975): Percutaneous absorption: on the relevance of in vitro data. *J Invest Dermatol.*, 64:190-195.
14. Schwartz, J. A., Lium, E. K., and Silverstein, S. J. (2001): Herpes simplex virus type 1 entry is inhibited by the cobalt chelate complex CTC-96. *J. Virol.*, 75:4117-4128.

I claim:

1. A method for reducing the severity of herpes labialis in a human subject comprising topically applying to the effected epidermal area of the subject, an anti-herpes labialis effective amount of the compound CTC-96, homogeneously mixed in a dermal ointment and sufficient to penetrate into the epidermal but not the dermal layer of the skin of the subject wherein the dermal ointment contains from 1 to 10 mg/g of CTC-96.

* * * * *